United States Patent
Davis et al.

(10) Patent No.: US 9,717,891 B2
(45) Date of Patent: Aug. 1, 2017

(54) SKIN DRESSING WITH ELECTRODES AND PHYSIOLOGICALLY ACTIVE PRECURSOR SUBSTANCE

(71) Applicant: Microarray Limited, Bedford (GB)

(72) Inventors: Paul Davis, Felmersham (GB); Andrew Austin, Great Addington (GB)

(73) Assignee: Microarray Limited, Sharnbrook (GB)

( * ) Notice: Subject to any disclaimer, the term of this patent is extended or adjusted under 35 U.S.C. 154(b) by 148 days.

(21) Appl. No.: 14/383,284

(22) PCT Filed: Mar. 21, 2013

(86) PCT No.: PCT/GB2013/050741
§ 371 (c)(1),
(2) Date: Sep. 5, 2014

(87) PCT Pub. No.: WO2013/140176
PCT Pub. Date: Sep. 26, 2013

(65) Prior Publication Data
US 2015/0025479 A1    Jan. 22, 2015

(30) Foreign Application Priority Data

Mar. 23, 2012 (GB) .................................. 1205120.7
Jun. 1, 2012 (GB) .................................. 1209820.8

(51) Int. Cl.
*A61N 1/30* (2006.01)
*A61M 35/00* (2006.01)
(Continued)

(52) U.S. Cl.
CPC .............. *A61M 35/00* (2013.01); *A61F 13/00* (2013.01); *A61F 13/00004* (2013.01);
(Continued)

(58) Field of Classification Search
CPC .......................... A61F 13/00; A61F 13/00004
(Continued)

(56) References Cited

U.S. PATENT DOCUMENTS 5,053,001 A   10/1991  Reller et al.
5,855,570 A   1/1999   Scherson et al.
(Continued)

FOREIGN PATENT DOCUMENTS

AU    2005205797 A1    9/2005
EP       1631328 B1    3/2007
(Continued)

OTHER PUBLICATIONS

English-language abstract of PCT Patent Application Publication No. WO 2011/099512 A1, European Patent Office, Aug. 18, 2011.
(Continued)

*Primary Examiner* — Amanda Patton
*Assistant Examiner* — Philip C Edwards
(74) *Attorney, Agent, or Firm* — Dascenzo Intellectual Property Law, P.C.; Ian D. Gates

(57) ABSTRACT

A skin dressing comprising first and second electrodes, an electrical power supply not electrically connected to either or both of the first and second electrodes, and further comprising a physiologically or antimicrobially active precursor substance, the dressing being operable, when placed on a skin site to be treated, to connect the electrical power supply to both the first and second electrodes, thereby to trigger the electrochemical oxidation or reduction of the precursor substance on one of the electrodes to produce a physiologically or antimicrobially active oxidized or reduced compound which is capable of diffusing towards the skin site for the treatment thereof.

20 Claims, 7 Drawing Sheets

(51) Int. Cl.
*A61N 1/04* (2006.01)
*A61F 13/00* (2006.01)
*A61K 9/00* (2006.01)

(52) U.S. Cl.
CPC ...... *A61F 13/00063* (2013.01); *A61K 9/0009* (2013.01); *A61N 1/044* (2013.01); *A61N 1/0436* (2013.01); *A61N 1/0468* (2013.01); *A61N 1/0496* (2013.01)

(58) Field of Classification Search
USPC .......................................................... 604/20
See application file for complete search history.

(56) References Cited

U.S. PATENT DOCUMENTS

| | | | |
|---|---|---|---|
| 6,490,482 B2 | 12/2002 | Mori et al. | |
| 2004/0267231 A1 | 12/2004 | Sun et al. | |
| 2005/0181026 A1 | 8/2005 | Davis et al. | |
| 2006/0025665 A1 | 2/2006 | Dupelle et al. | |
| 2007/0112294 A1 | 5/2007 | Akiyama et al. | |
| 2008/0004564 A1* | 1/2008 | Smith | A61N 1/303 604/20 |
| 2012/0310143 A1* | 12/2012 | Yaegashi | A61N 1/0428 604/20 |

FOREIGN PATENT DOCUMENTS

| | | | | |
|---|---|---|---|---|
| EP | 1932562 A1 | 6/2008 | | |
| JP | 2001-521798 | 11/2001 | | |
| JP | 2007-75327 | 3/2007 | | |
| JP | WO2011099512 | * 8/2011 | ............... | A61N 1/30 |
| WO | WO 99/22810 | 5/1999 | | |
| WO | WO 01/96422 A1 | 12/2001 | | |
| WO | WO 03/090800 A1 | 11/2003 | | |
| WO | WO 2004/105865 A1 | 12/2004 | | |
| WO | WO 2004/108917 A1 | 12/2004 | | |
| WO | WO 2005/072783 A1 | 8/2005 | | |
| WO | WO 2006/095193 A2 | 9/2006 | | |
| WO | WO 2011/099512 A1 | 8/2011 | | |

OTHER PUBLICATIONS

Search Report issued in connection with United Kingdom Patent Application No. GB1205120.7, 1 page, United Kingdom Intellectual Property Office, Jul. 11, 2012.

English-language abstract of PCT Patent Publication No. WO 99/22810, which corresponds to Japan Patent No. JP 2001-521798, European Patent Office, Nov. 13, 2001.

English-language abstract of Japan Patent No. JP 2007-75327, European Patent Office, Mar. 29, 2007.

A World of Beauty webpage, http://www.topsalons.ru/2234.html, 2008-2010, retrieved May 10, 2017.

English language translation of A World of Beauty webpage, http://www.topsalons.ru/2234.html, 2008-2010, retrieved May 10, 2017.

Landsberg G.S., Textbook of Elementary Physics, vol. II, Electricity and Magnetism, "Science," Moscow, 1975, p. 170.

English language translation of Landsberg G.S., Textbook of Elementary Physics, vol. II, Electricity and Magnetism, "Science," Moscow, 1975, p. 170.

Ushakov A.A., Practical Physical Therapy, MIA, Moscow, 2009, pp. 27 and 29.

English language translation of Ushakov A.A., Practical Physical Therapy, MIA, Moscow, 2009, pp. 27 and 29.

* cited by examiner

SKIN DRESSING WITH ELECTRODES AND PHYSIOLOGICALLY ACTIVE PRECURSOR SUBSTANCE

TECHNICAL FIELD

The present invention relates to a skin dressing for the treatment of a human or animal skin or wound site.

BACKGROUND AND PRIOR ART

Delivery of physiologically or antimicrobially active chemical species to provide a medical benefit to a skin site, e.g. a wound, is of continuing interest.

A convenient route for delivery is via a skin dressing, typically packaged and available for use by the end user for direct topical application as desired.

However a large number of physiologically or antimicrobially active species are difficult to administer from such a skin dressing. A particular difficulty arises when the active species is highly reactive and therefore unstable with a short shelf life.

One way to overcome this problem of reactivity is to generate the physiologically active species in the dressing shortly before or during application of the skin dressing. In this way, stable precursor materials are converted into reactive materials only when they are needed.

WO 03/090800 discloses a skin dressing where hydrogen peroxide is generated within a dressing through the action of an enzyme and atmospheric oxygen.

WO 2006/095193 discloses a dressing where reactive and unstable nitric oxide is generated in a skin dressing during use.

However one problem with this approach is that the dressings tend to be more complex than widely used inactive dressings, often requiring separate components to be brought together at the moment of use. The need for oxygen to be available for the enzyme is another problem, especially when the enzyme-containing dressing is covered by a protective film or outer bandage.

It would therefore be highly desirable to develop a skin dressing which is able to deliver reactive physiologically active species and is more convenient to use.

SUMMARY OF THE INVENTION

Skin dressings comprise first and second electrodes, an electrical power supply electrically connected to both of the first and second electrodes, a precursor substance, and a physiologically or antimicrobially active compound produced by the electrochemical oxidation or reduction of the precursor substance on one of the first electrode and the second electrode.

Methods of applying skin dressings to a skin site comprise providing a skin dressing comprising first and second electrodes, an electrical power supply not electrically connected to at least one of the first and second electrodes, and a precursor substance; placing the skin dressing on the skin site; connecting the electrical power supply to at least one of the first and second electrodes to form an electrochemical circuit; and producing a physiologically or antimicrobially active compound by the electrochemical oxidation or reduction of the precursor substance on one of the first electrode and the second electrode.

DESCRIPTION

Figure 1:
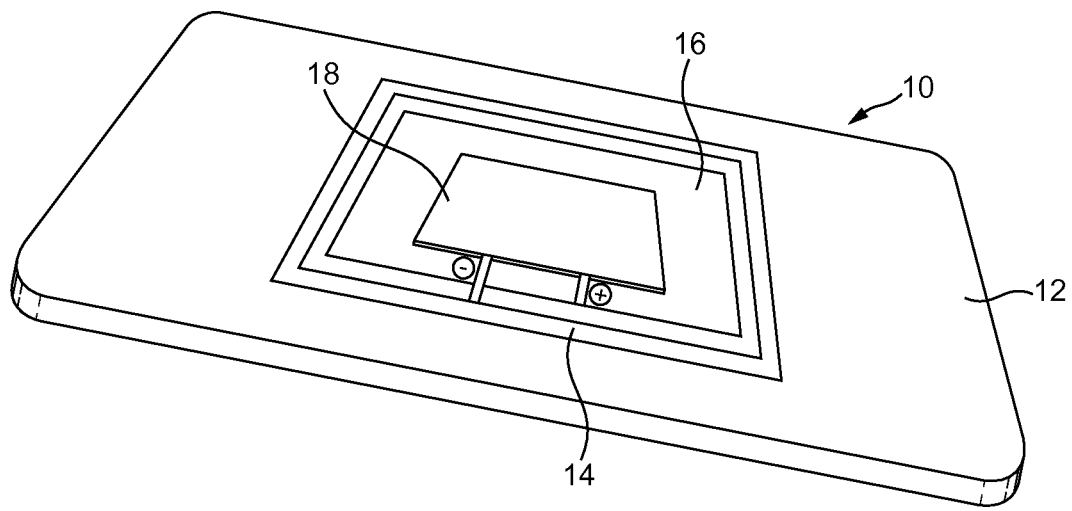
FIG. 1 is a schematic representation of a skin dressing according to the invention.

The present invention relates to a skin dressing comprising first and second electrodes, an electrical power supply not electrically connected to either one or both of the first and second electrodes, and further comprising a physiologically or antimicrobially active precursor substance, the dressing being activatable, when placed on a skin site to be treated, by connection to the electrical power supply to both the first and second electrodes, thereby to trigger the electrochemical oxidation or reduction of the precursor substance on one of the electrodes to produce a physiologically active oxidised or reduced substance which is capable of diffusing towards the skin site for the treatment thereof.

Thus, the skin dressing remains in an inactive and stable state with the electrodes not electrically connected to each other and the precursor substance ready to be converted upon use. When it is desired to use the dressing, the electrical connection is made which starts the electrochemical conversion of the precursor to the physiologically or antimicrobially active chemical species. Once produced, the active species is then free to diffuse or be otherwise transported to the skin site to be treated.

In this way, the present invention seeks to generate the physiologically or antimicrobially active species only during use but also achieves this with greater reliability, control and flexibility.

The electrodes are typically sheet-like and substantially planar. Preferably the electrodes have a thickness of less than 1.0 mm, more preferably less than 0.5 mm.

The electrodes are preferably co-planar, to ensure that the electrochemical production of active agents is focussed within a zone of the dressing from which diffusion into the skin or wound site can be controlled.

In a preferred embodiment the electrodes are printed on a single sheet of material. This arrangement makes it possible to enhance the bulk manufacturing process by printing multiple electrodes on a continuous sheet for reel-to-reel processing.

Typically, an antimicrobially or physiologically active species will be generated on either the cathode or the anode only. Therefore it is generally desirable to optimise the electrode geometry to ensure that the antimicrobially or physiologically active species are produced uniformly over the whole surface of the generator electrode into the desired area of activity.

Thus, preferably the ratio of the surface area of the first electrode to the second electrode is at least 2:1, more preferably at least 4:1, most preferably at least 8:1. This provides a large surface area for the electrode at which the antimicrobially or physiologically active species is generated.

In the preferred case where the electrodes are coplanar and one electrode has a higher surface area than the other, it becomes a challenge to ensure that sufficient current passes through the entirety of the larger electrode. If steps are not taken to distribute the current flow through the larger electrode, an uneven electrical potential will exist on the surface of the electrode, leading to uneven generation of the antimicrobially or physiologically active species.

One way in which good electrical contact can be made between two co-planar electrodes, is to arrange one electrode to substantially surround the other electrode. It has been found that this can be achieved irrespective of whether the electrode being surrounded is the one with a greater surface area or not.

It would also be desirable if the electrodes could be designed in such a way that they could be trimmed to a shape and size by the user to match the shape and size of the wound or skin site, e.g. by trimming with a blade or pair of scissors, and still function as electrodes with unencumbered electron flow between them. However when one electrode substantially surrounds the other electrode, it is possible that such trimming will remove proportionally more of one electrode than the other and could have a severely deleterious effect on the functioning of the circuit.

One way in which this trimming can be achieved without disrupting the integrity and balance of the remaining elements is to provide the electrode having a smaller surface area in the form of multiple strands or elements, which are arranged to spread apart from each other. In this way, even if one strand or element is removed entirely, at least one other will remain intact, connected to the power supply in balance association with its counterpart provided it is spread apart from the one lost to trimming.

Although metallic electrodes would provide an effective electrical circuit with the least resistance, it has been found that this is undesirable because such electrodes can corrode. It has therefore been discovered that non-metallic electrodes, even with their reduced conductivity in comparison to metallic electrodes, are preferred. Moreover, the reduced conductivity has been found to be advantageous in slowing down the electrochemical reaction so that the antimicrobially or physiologically active species can be delivered at an optimised rate, over a longer period of time. Thus the electrodes are preferably non-metallic, e.g. made from carbon, although a wide variety of non-metallic materials are possible.

In one preferred embodiment the precursor compound is an iodide salt. When the electrodes are electrically connected to each other the negatively charged iodide ions (anions) migrate to the positively charged working electrode. Once there the iodide donates an electron and is oxidised to iodine. Iodine is a well-known physiologically active compound and a potent antimicrobial agent.

In another preferred embodiment the precursor compound is a sulphate ($SO_4^{2-}$) salt. When the electrodes are electrically connected to each other, the negatively charged sulphate ions (anions) migrate to the positively charged working electrodes. Once there they then donate an electron and are oxidised to peroxodisulphate ($S_2O_8^{2-}$). Peroxodisulphate spontaneously decomposes to produce hydrogen peroxide, a highly potent and reactive physiological or antimicrobial agent.

The potential difference applied to the electrodes depends on the redox potential of the species being oxidised or reduced. For example, if iodide is being oxidised then the potential must be greater than +0.55V and if sulphate is being oxidised then it should preferably be greater than 2.0V.

In practice the voltage applied will be greater than the minimum value, to ensure reasonable kinetics for the reaction. Thus, voltages of from 1 to 10 volts, are preferably applied, more preferably from 2 to 5 volts are applied.

The skin dressing is typically packaged for optimal performance prior to use, e.g. being sealed in suitable sterile water-impervious packages, e.g. of laminated aluminium foil.

When the dressing is to be unpacked and used, the electrical connection is made between the two electrodes. In one particularly convenient embodiment, the connection is made by removal of an insulating tab. The removal of the tab may be by separate action of the user or it could be triggered by removal of the skin dressing from its packaging.

The skin dressing also comprises a skin-contact layer, which acts as the diffusion medium for the produced active species and a reservoir of the precursor substance, as well as physically separating the electrodes from the skin or wound surface.

Typically the electrodes will be on top of, or embedded within, the skin-contacting layer.

The components of the skin-contact layer are constructed of a material that can be dispensed as a coherent entity, whether in sheet (or film) form, or as an amorphous gel (e.g. that can be squeezed from a dispenser) and which will stay in place when applied to a target site (e.g. a wound or an area of skin).

The form of the skin contact layer may be selected to suit the intended use, e.g. the component is conveniently in the form of a sheet, layer or film. The layer or film typically has a thickness in the range 0.01 to 2.0 mm, preferably in the range 0.05 to 1.0 mm.

The skin-contacting layer is typically in a hydrated condition, which means that it contains sufficient water for the electrochemical circuit to be formed and for the generated active species to diffuse through its structure and to target, e.g. wound or skin.

Additionally, skin dressing provides a source of moisture which can act in use to maintain a beneficial moist environment within a target wound site.

The material of the skin-contacting layer may be in the form of hydrogel, a sponge, a foam or some other form of hydrophilic matrix that can hold sufficient water to allow a controlled diffusion path from the electrodes to the target site.

The skin-contacting layer can control active species flux rates in numerous ways, including by selection of its physical dimensions (especially depth, affecting diffusion path distance), its extent of cross-linking (affecting the rate of solute diffusion) its water content (less water causing a slower diffusion rate), its composition (with immobilised hydrogen bonding groups slowing hydrogen peroxide movement) and/or its surface architecture at the interface with the target site, e.g. wound site, and/or at the interface with the upper component (affecting the contact surface areas and thereby the rate of transfer into or out of the lower component), e.g., it may have a contoured (possibly corrugated) surface.

Typically, skin or a wound is in direct contact with the skin-contacting layer. The skin-contacting layer, preferably when in the form of a hydrated hydrogel as discussed below, can (depending on its chemical composition) act to absorb water and other materials exuded from a wound site, enabling the dressing to perform a valuable and useful function by removing such materials from a wound site.

The skin-contacting layer may alternatively be in the form of an amorphous gel or lotion, preferably a hydrogel, not having a fixed form or shape, that can be deformed and shaped in three dimensions, including being squeezed through a nozzle. Amorphous gels are typically not cross-linked or have low levels of cross-linking. A shear-thinning amorphous gel may be used. Such a gel is liquid when subjected to shear stress (e.g. when being poured or squeezed through a nozzle) but is set when static. Thus the gel may be in the form of a pourable or squeezable component that may be dispensed, e.g. from a compressible tube or a syringe-like dispenser, comprising a piston and cylinder, typically with a nozzle of about 3 mm diameter. Such a gel may be applied in the form of a surface layer, or into a wound cavity as a fully conformable gel that fills the available space and contacts the wound surface.

A further alternative form through which to achieve this function is that of a firm cross-linked gel that has been comminuted to form a conformable mass of closely juxtaposed fine particles that behave cohesively as an amorphous solid, retaining the overall properties of the particles from which it is formed.

This approach finds particular application in the treatment of cavity wounds by, for example, squeezing from a tube or syringe. Once an appropriate mass of amorphous gel has been placed in the cavity, a thin electrode assembly is pushed into the gel. The battery is associated with a cover film with which to close off the entrance to the cavity. Once in place, the circuit is completed by making an electrical connection between the battery and electrode. Alternatively, the amorphous gel can be supplied in bolus form, contained within a porous 'stocking' with the electrode, battery and cover film already assembled and in place.

It is also possible for the material to be carried in the form of a dry rope or tape assembled with the electrical components, ready to be packed into a cavity. On wetting of the upper component, e.g. by deliberate addition of water, the material becomes hydrated and able to conduct an electrical current. If, for example, the gel includes iodide ions then passage of the current will lead to iodine generation within the gel.

A typical example of an amorphous hydrated hydrogel formulation is: 15% w/w AMPS (sodium salt), 5% w/w glucose, 0.05% w/w potassium iodide, 0.1% zinc lactate, 0.19% polyethylene glycol diacrylate and 0.01% hydroxycyclohexyl phenyl ketone, with the volume made up to 100% with analytical grade DI water. The reagents are thoroughly mixed and dissolved, then polymerised for between 30-60 seconds, using a UV-A lamp delivering approximately 100 mW/cm$^2$, to form the required hydrogel. This may be in the form of a flat sheet or, more conveniently, housed in plastic syringes. The amorphous gel may then be dispensed from a syringe into a target site.

A hydrated hydrogel means one or more water-based or aqueous gels, in hydrated form. A hydrated hydrogel can act to absorb water and other materials exuded from a wound site, enabling the dressing to perform a valuable and useful function by removing such materials from a wound site. The presence of glucose further enhances the osmotic strength of the gel, helping it to take up fluid from the wound, as well as providing an energy source for the cells engaged in healing the wound. The hydrated hydrogel also provides a source of moisture, that can act in use to maintain a wound site moist, aiding healing. The hydrated hydrogel also acts as a source of water, causing release of hydrogen peroxide. Use of a hydrated hydrogel has other benefits as discussed in WO 03/090800.

Suitable hydrated hydrogels are disclosed in WO 03/090800. The hydrated hydrogel conveniently comprises hydrophilic polymer material. Suitable hydrophilic polymer materials include polyacrylates and methacrylates, e.g. available commercially in the form of proprietary sheet hydrogel dressings, including poly 2-acrylamido-2-methylpropane sulphonic acid (polyAMPS) or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BF from ISP Europe), poly(methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

In a hydrated hydrogel of hydrophilic polymer material, the hydrophilic polymer material is desirably present at a concentration of at least 1%, preferably at least 2%, more preferably at least 5%, yet more preferably at least 10%, or at least 20%, desirably at least 25% and even more desirably at least 30% by weight based on the total weight of the gel. Even higher amounts, up to about 40% by weight based on the total weight of the gel, may be used.

A preferred hydrated hydrogel comprises poly 2-acrylamido-2-methylpropane sulphonic acid (poly AMPS) or salts thereof, preferably in an amount of about 30% by weight of the total weight of the gel.

The skin-contacting layer can be manufactured by known means. Preferably it is manufactured by the polymerisation of AMPS monomer dissolved at the rate of about 40% w/v in a solution buffered to a pH of about 5.5, containing any further ingredients required for controlling the rate of transmission or reaction of oxidised or reduced chemical substance such as iodine. Typically, the iodide concentration should be about 0.01-0.2% w/v. If a stronger antimicrobial effect is required then the level of iodide should be from about 0.05% to about 0.2% w/v together with a higher applied voltage (e.g. 5.0 volts). Methods for the manufacture of this material are as described in patent number EP1631328.

In addition, the dressing may incorporate one or more other active ingredients such as zinc ions, as disclosed in WO 2004/108917. Zinc ions are known to be an essential nutritional trace element with numerous functions in the growth and repair of living tissues.

Lactate ions may be included in the skin dressing. Lactate ions have a mild buffering effect within the delivery system. Lactate ions are also believed to have an important role in stimulating angiogenesis—the growth and regeneration of new blood vessels.

A source of glucose is preferably included in the skin dressing. In addition to its role as a respiratory substrate, glucose is believed to participate (as a metabolic precursor) in building polysaccharides of various types that form extracellular matrix (ECM), essential to tissue repair and healing. Preferred skin-contacting layers of this sort are disclosed in our European Patent Application No. 04250508.1 and British Patent Application No. 0427444.5.

In a further refinement, the skin dressing can also contain a sensing means, for sensing the concentration of a particular marker. The sensor can then be arranged to sense for protease activity, pH or temperature, for example. Furthermore, the output of the sensor could be coupled to the electrical power supply, possibly altering the power supply voltage in accordance with the level of detected marker. In this way, if the sensor detected infection (e.g. from certain patterns of protease activity) it could increase the applied voltage, which would thereby increase the rate of iodine generation, for example.

Another type of sensor-controlled iodine delivery can be achieved by means of an in-dressing iodine sensor, such that the voltage is reduced appropriately when a particular (i.e. optimum) concentration of iodine has been generated.

Turning to the figures, FIG. 1 shows a skin dressing 10, comprising a skin-contacting layer 12, a first electrode 14, a second electrode 16 and a battery 18. The first electrode 14 is made of flexible carbon and is approximately 0.5 mm thick and square shaped. The second electrode 16 is similar to the first electrode 14 but is smaller in its square dimension.

The battery 18 is also very thin having a thickness of around 0.5 mm and is connected to both the first electrode 14 and second electrode 16 but for an insulating tab (not shown) which prevents the electrical connection between the electrodes.

In use the skin dressing 10 is removed from packaging, which also acts to remove the insulating tab (not shown). This creates an electrical connection between the electrodes and sets up an electrochemical circuit.

The skin-contacting layer 12 contains a precursor compound, such as iodide or sulphate, which is oxidised electrochemically to produce a physiologically active species such as iodine or hydrogen peroxide, which diffuses through the skin-contacting layer 12 to the skin site to be treated.

Figure 2:
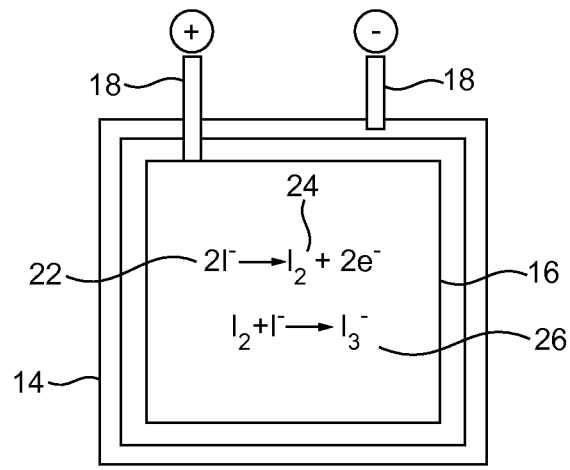
FIG. 2 is a schematic representation of the electrodes and power supply for use in the present invention.

FIG. 2 shows in greater detail the electrodes 14, 16 together with their connections to the electrical power supply 18. Also shown is a reaction scheme showing how iodide is electrochemically oxidised to iodine, which also further reacts to form a tri-iodide complex 26, which is also physiologically active.

EXAMPLES

Example 1

A crosslinked polymeric hydrogel containing iodide ions, was placed onto an electrochemical sensor. The hydrogel was approximately 5 cm×5 cm×0.25 cm. The electrochemical sensor was of a 3 electrode design, constructed from 3 screen printed carbon tracks, with large counter, small working (approximately 2 mm diameter) and silver/silver chloride reference electrodes. The sensor was connected to an Ezescan potentiostat (Whistonbrook Technologies, Luton, UK) and ran using the accompanying Ezescan software.

Two screen printed carbon electrodes were placed onto the upper surface of the exposed hydrogel, where the one being used as the anode was located directly above the working electrode on the electrochemical sensor. The cathode was placed close to, but not touching, the anode. The anode and cathode carbon electrodes were connected to batteries to provide either 1.5, 3 or 5 volts. Detection of molecular iodine was performed on the working electrode of the electrochemical sensor, using chronoamperometry with the potential poised at −100 mV vs the silver/silver chloride reference. Once the chronoamperometric method was started, the batteries were turned on, and the experiment left to run for 1000 mins.

Figure 3:
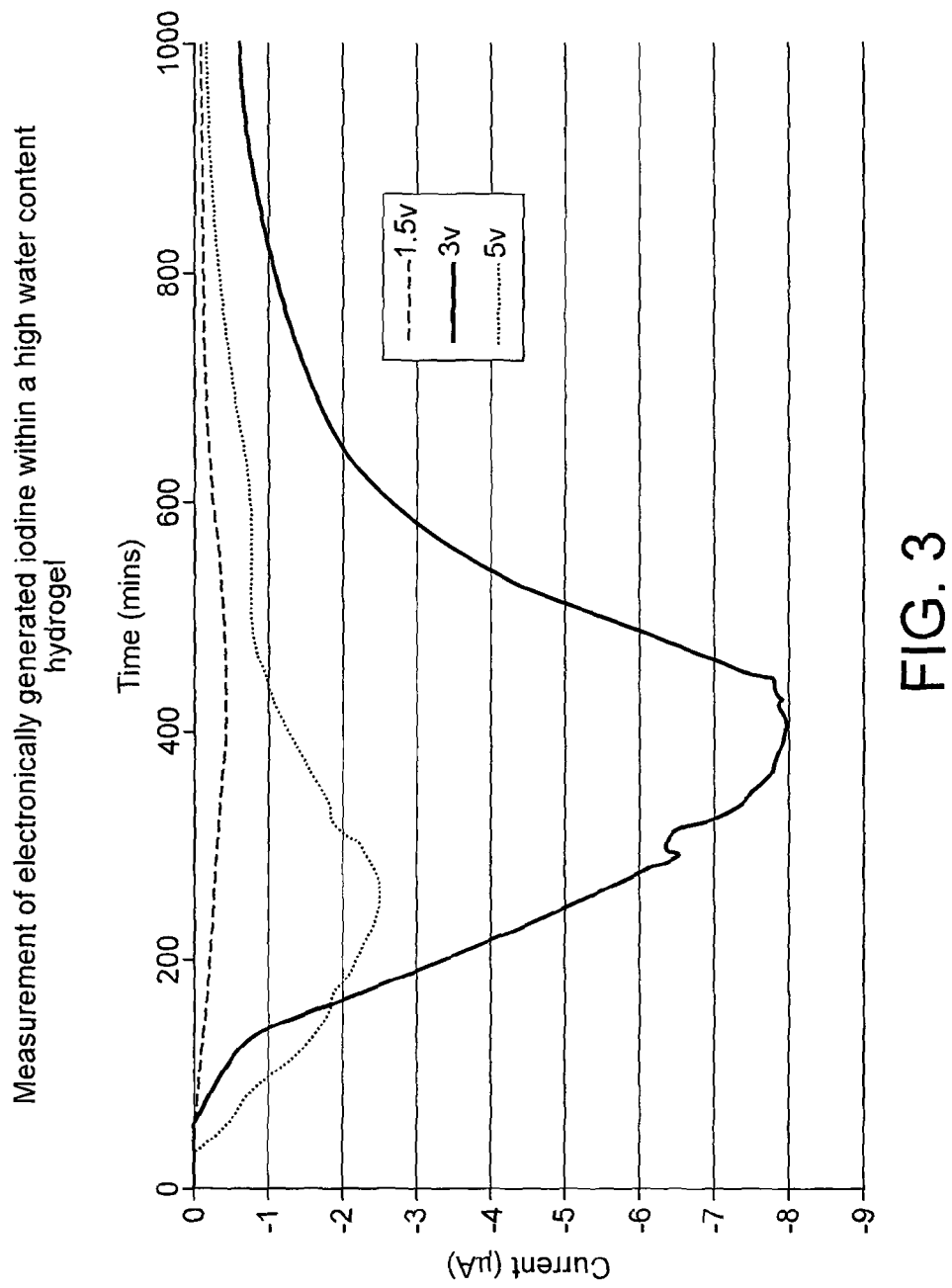
FIG. 3 is a chart showing measured current versus time for the detection of iodine using chronoamperometry in an arrangement according to the present invention.

After approximately 450 minutes, the batteries were disconnected. The presence of iodine at the working electrode, where iodine is reduced to iodide, is measured as a change of current. FIG. 3 demonstrates the measurement of iodine at the working electrode. In all cases, there was a change in current, indicating molecular iodine was being measured, which in turn confirms the generation of iodine via the battery electrodes on the surface of the hydrogel.

The presence of iodine was confirmed visually, where the hydrogel was a deep orange/brown colour under and around the anode. The smallest peak current was obtained with the smallest battery voltage, while the largest was obtained with the 3 v battery voltage. The 5 volt battery gave a peak iodine concentration of between the highest (3 v) and lowest (1.5 v). This is believed to be due to the over production of iodine at the battery anode, leading to fouling of the carbon surface, reducing the efficiency of the iodide to iodine conversion.

Example 2

Four hydrogel variations were prepared with sodium sulphate at 50 mM, and with pH buffered at 7, 6, 5 and 4 (citrate buffer). Voltages of 2.5V and 5 V were applied to pieces of the four hydrogel variants through a carbon film electrode for 15, 30, 45, 60 and 120 minutes.

Tests were carried out on each gel type at each time interval to determine the presence of hydrogen peroxide by means of a standard starch iodide reagent. Duplicate gel pieces were also tested with an oxygen electrode to determine the amount of oxygen dissolved in the hydrogel.

The results showed that hydrogen peroxide was produced at a useful rate in all of the gel types (i.e. at each of the pH values) and that the amount increased steadily over the time period of the test. Raised levels of oxygen were found in each gel piece tested, and the levels reached saturation with longer times of electrochemical reaction.

Example 3

Iodide (for example potassium iodide) will undergo oxidation to form iodine. In an electrochemically driven oxidation, this will occur at potentials of over approximately +400 mV (relative to silver/silver chloride reference electrode) via the following equation:

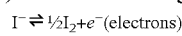

$$I^- \rightleftharpoons \tfrac{1}{2}I_2 + e^- \text{(electrons)}$$

This oxidation will accelerate if the potential is increased. The generation of iodine via the electrochemical oxidation of iodide was demonstrated using a graphite carbon/carbon black electrode system.

In general, two electrodes, which acted as the anode and cathode, were positioned on an iodide-containing hydrogel, and a potential of +3.2V was applied. Iodine was generated at the anode, as seen by the change in colour from colourless (iodide) to orange (iodine).

Figure 4:
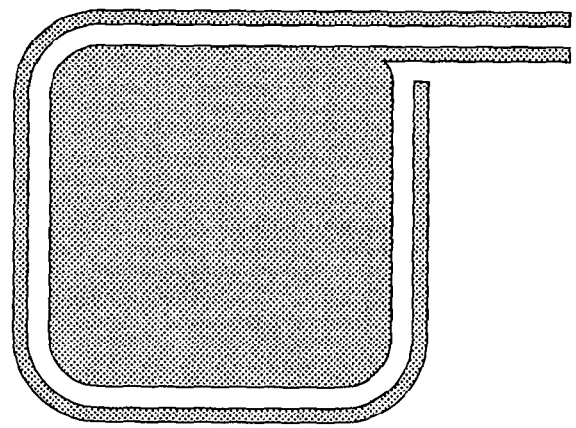
FIG. 4 is a representation of electrode assembly design 1, which has a large central area used as the anode, with the smaller outer track used as the cathode.
Figure 5:
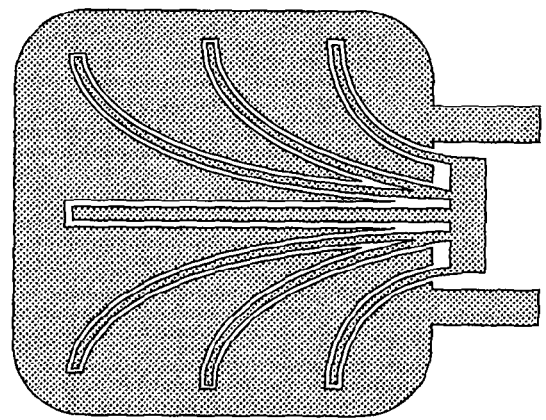
FIG. 5 is a representation of electrode assembly design 2, which has a large outer area used as the anode, with the inner fanned tracks used as the cathode.

In detail, electrodes of two specific designs (Archimed LLP) were screen printed onto a polyester backing by Jaybee Graphics Ltd, using an electrically conductive carbon paste (Acheson Electrodaq 423SS). The surface area of the anode was larger than the cathode, to increase the area of iodine generation. See FIGS. 4 and 5.

Figure 6:
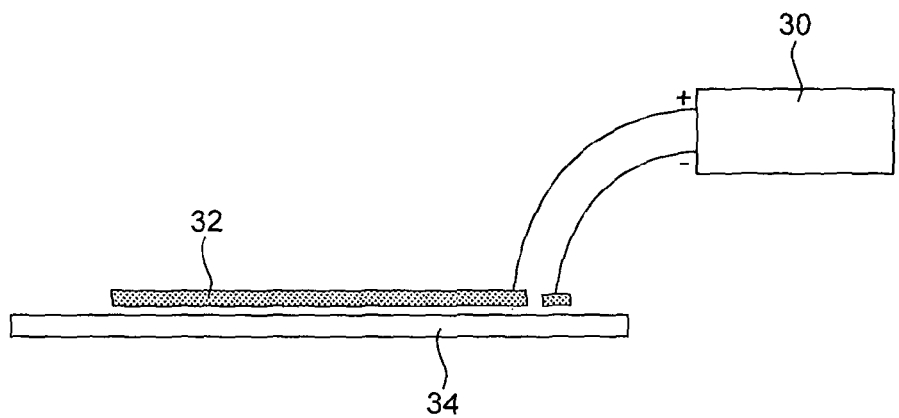
FIG. 6 is a schematic representation of a basic set-up of a hydrogel and electrode assembly.

The individual electrode assemblies (consisting of the anode and cathode) were placed onto an iodide containing hydrogel (e.g. Iodozyme™ anti-microbial wound dressing (Archimed LLP)) in a central position, with the carbon in contact with the hydrogel surface. Battery packs containing 2×1.6V AA batteries (therefore a total of 3.2V) were attached to the anode and cathode of both examples and switched on. See FIG. 6, wherein 2×1.6 v batteries 30 are connected to the electrode assembly 32 on top of a hydrogel 34. The battery packs 30 were left attached for 3 hours before removal. The electrode assemblies were removed and the development of iodine examined.

Figure 7:
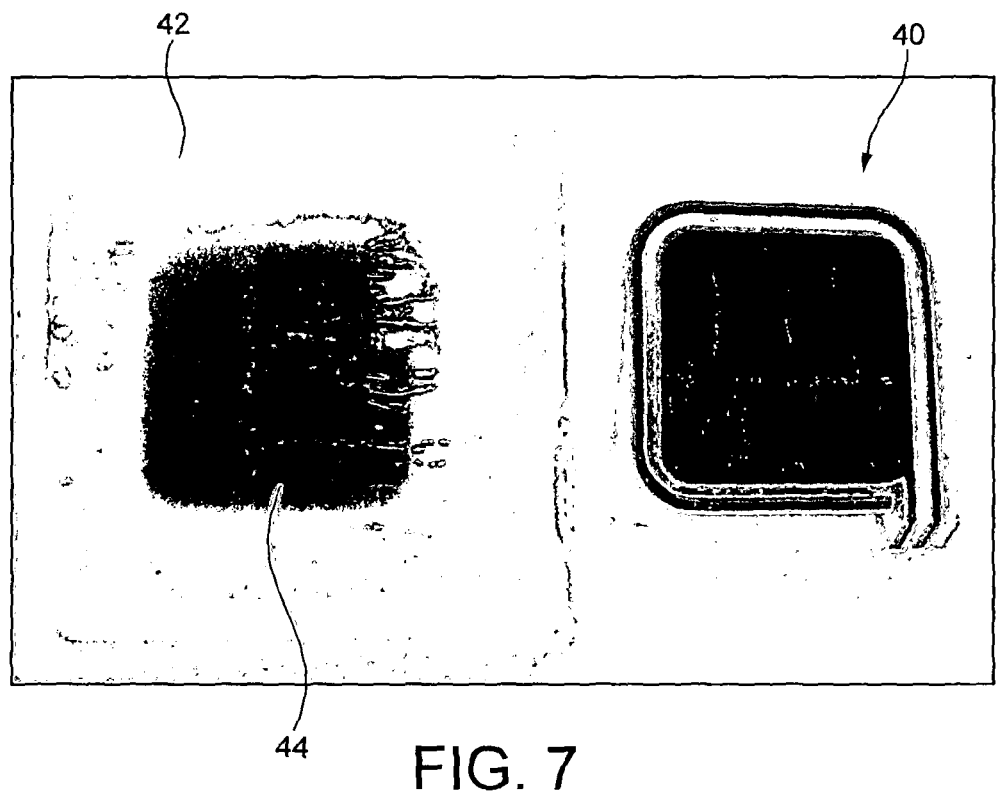
FIG. 7 shows images of the electrode design 1 and the resulting coloured hydrogel from iodine formation in use.

FIG. 7 shows an image of electrode design 1 40 together with the hydrogel 42 it was in contact with during use. It can be seen that an even generation of iodine had occurred across the complete surface area of the large anode at patch 44. Iodide had been oxidised at the surface of the carbon electrode, with electron transfer from the iodide molecules to the positively charged anode.

Figure 8:
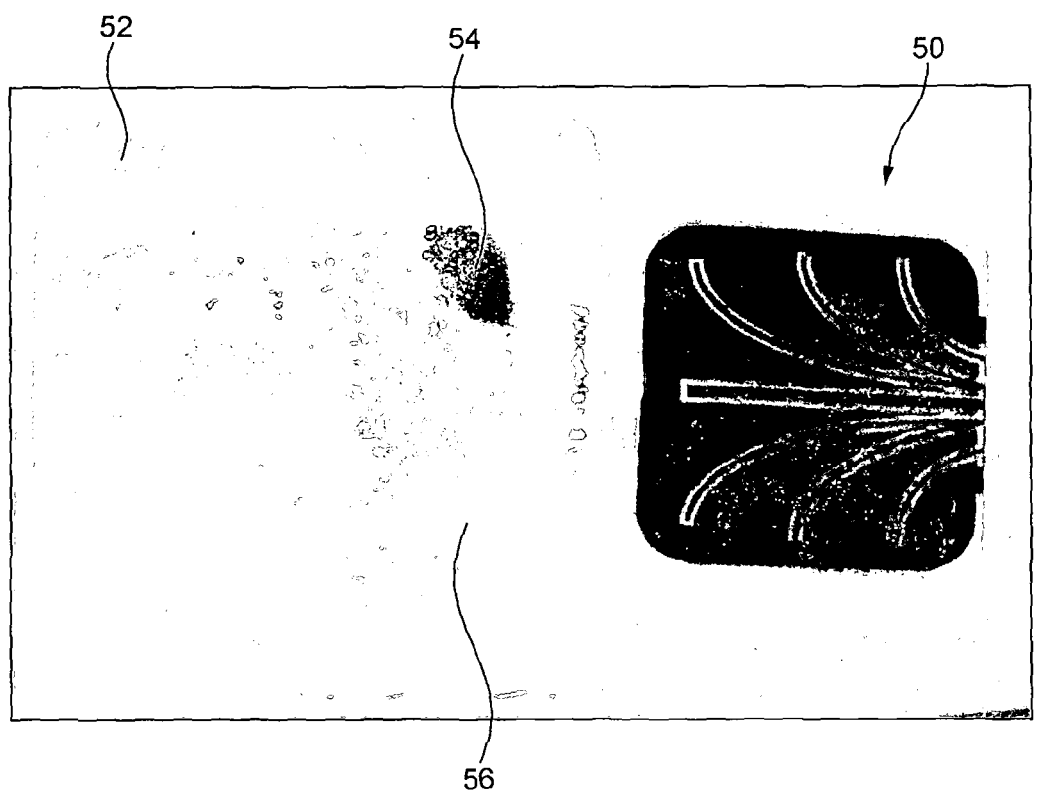
FIG. 8 shows images of the electrode design 2 and the resulting coloured hydrogel from iodine formation in use.

FIG. 8 shows an image of electrode design 2 50 together with the hydrogel 52 it was in contact with during use. Interestingly, the development of iodine was very much more evident as a gradient, with the highest iodine concentration 54 nearest to the point of anode contact with the battery, and the weakest iodine concentration 56 the furthest point. This is explained when the design of the electrode assembly is examined. With electrode design 1, the anode is presented as an uninterrupted surface, with the cathode positioned around the outer edge of the anode.

This design thus allows the current to flow in a uniform manner throughout the entire electrode surface, allowing even generation of iodine. In electrode design 2, the anode is not an uninterrupted surface, with the cathode elements interspersed within the anode. Due to the electrical resistance of the screen printed carbon electrodes (which increases with distance), the potential relative to the battery terminals drops with an increase in distance from the battery terminals. While the same is true for design 1, the distance in design 2 can be measured to be significantly more, thus this electrode design was able to show the effect of distance on the relative electrode potentials and the subsequent decreased efficiency of iodine generation.

In addition, it was also observed that the area of contact closest to the position where the battery connections to the electrode assembly were made, produced a localised area of high iodine concentration, as seen by a dark orange colour (labelled 54 in FIG. 8). This would indicate the propensity for the current flow to take the route of least resistance (i.e. closest to the electrode connection points) and also the point of highest potential (relative to the rest of the electrode). Both these factors therefore allow the highest turnover of iodine compared to the overall electrode assembly. One interesting outcome of this observation, would be an improved design of electrode whereby there are many local "hotspots" of iodine generation, such as an array, that would allow an improved efficiency of iodine generation.

It was clearly demonstrated that with the interspersed design there are large changes of potential present which affect the oxidation of iodine. FIG. 8 demonstrated how changing the potential spread within the electrode changed the iodine generation profile. To examine the effect of multiple battery connection points to the electrode assembly, the battery was connected to the anode in two different places (instead of just one as seen in FIG. 8), and after 3 hours, the spread of iodine was evaluated and compared to FIG. 8.

Figure 9:
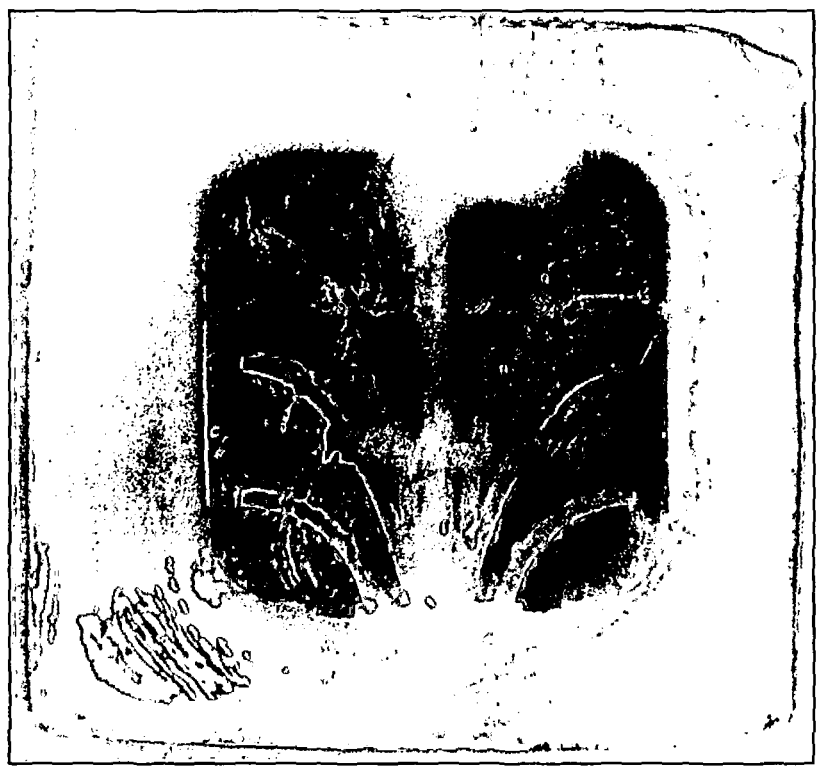
FIG. 9 is another image of the resulting coloured hydrogel from iodine formation when electrode design 2 is used.

FIG. 9 demonstrates the effect of two connection points made to the anode. The figure clearly shows that the two connection points had improved the generation of iodine throughout the entire dressing. This is due to the increase in localised potential due to the reduction of distance current has to flow through the anode carbon to complete the circuit. By improving the design of the electrode, a clear improvement in the generation and spread of iodine was achieved. It was therefore demonstrated that the design of the electrode was fundamentally important to achieve improved iodine spread and concentration.

Figure 10:
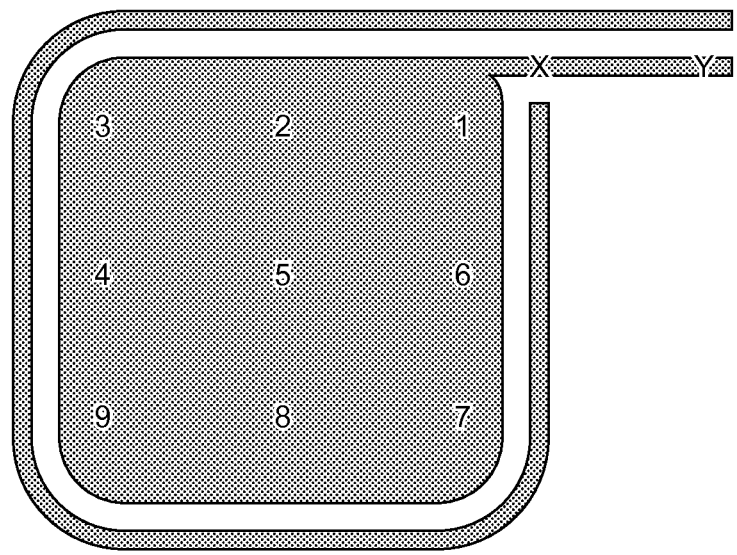
FIG. 10 is a representation of electrode design 1 and the positions of measurement of the electrical resistance throughout the carbon electrode, with reference to the point marked "X".
Figure 11:
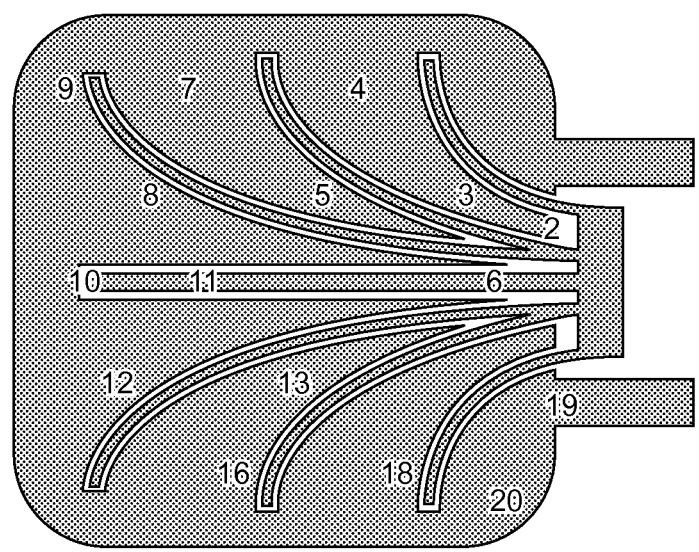
FIG. 11 is a representation of electrode design 2 and the positions of measurement of the electrical resistance throughout the carbon electrode, with reference to the point marked "2".

Electrode Resistance Map:

Electrode designs 1 and 2 were measured for resistance through the carbon surfaces. The points of measurement are shown in FIGS. 10 and 11.

With electrode design 1 (FIG. 10), the resistance was measured from the point marker "X".

TABLE 1 resistance values through the carbon electrode taken from electrode design 1.

| Measurement point (from point "X") | Resistance (Ohms) |
| --- | --- |
| 1 | 785 |
| 2 | 994 |
| 3 | 1147 |
| 4 | 1110 |
| 5 | 1014 |
| 6 | 993 |
| 7 | 1135 |
| 8 | 1095 |
| 9 | 1196 |
| Y | 1680 |

Table 1 shows the resistance values measured from point "X" in FIG. 10. As can be seen, apart from point 1, the other measurement points are all quite similar in their resistance values. This helps explain why the iodine colour seen in FIG. 7 is even. Ohms Law states V=IR (where V=voltage, I=current and R=resistance), therefore if the input voltage is constant (3.2V from the batteries) and the resistance values are all close, then the current through the electrode system will also be relatively uniform.

The resistance value measured from point X to point Y was surprisingly high, at 1680 ohms. The physical distance was measured to be 2 cm, and when comparing to the map in FIG. 10, where a number of points are also 2 cm apart, the resistance is high. A second resistance map of electrode design 1 was performed, but using point 1 as the reference point (see Table 2).

TABLE 2 resistance values through the carbon electrode taken from electrode design 1.

| Measurement point (from point "1") | Resistance (Ohms) |
| --- | --- |
| 2 | 385 |
| 3 | 527 |
| 4 | 511 |
| 5 | 410 |
| 6 | 391 |
| 7 | 533 |
| 8 | 485 |
| 9 | 581 |

The map in Table 2 clearly demonstrates the resistances throughout the anode electrode dropped significantly. This is due to the restrictive nature of the thin carbon strip (from X to Y) now not being part of the electrode. This suggests that the best design for the electrode should contain a large contact area with the battery (on the anode), to enable the resistance to be as low as possible.

With electrode design 2, a similar resistance map was constructed. FIG. 11 shows the points where measurements were taken, all relative to the static position marked "2".

TABLE 3 resistance values through the carbon electrode taken from electrode design 2.

| Measurement point (from point "2") | Resistance (Ohms) |
| --- | --- |
| 1 | 639 |
| 3 | 431 |
| 4 | 991 |
| 5 | 1199 |
| 6 | 1950 |
| 7 | 1543 |
| 8 | 1640 |
| 9 | 1880 |
| 10 | 2200 |
| 11 | 3250 |
| 12 | 2590 |
| 13 | 3620 |
| 14 | 2980 |
| 15 | 3320 |
| 16 | 3520 |
| 17 | 3870 |
| 18 | 4050 |
| 19 | 4800 |
| 20 | 4440 |

Table 3 shows the resistance valves through the electrode design 2. Even though the overall footprint of electrode design 1 and design 2 are the same, the resistance map clearly highlights the very large differences seen across the electrode. The localised hotspot of iodine (54 in FIG. 8) was due to the low resistance as measured at point 3. In general, as the resistance passes approximately 3000 ohms (points 14-20), the iodine generation is very low, as seen in FIG. 8. This therefore indicates that having the cathode inserts in the anode does not allow for an even flow of current throughout the whole of the anode.

Key Conclusions Drawn from this Work are as Follows:

The flow of current throughout the whole of the anode should be as unrestricted as possible. The connection point for the battery to the anode of the electrode should be as large and broad as possible. To increase efficiency of the electrode in the oxidation of iodide to iodine, the resistance of the anode should be as low as possible. Design of the electrode plays an important part in this.

The invention claimed is:

1. A skin dressing comprising first and second electrodes, an electrical power supply not electrically connected to either one or both of the first and second electrodes, and further comprising an inactive precursor substance for a physiologically or antimicrobially active substance, the dressing being activatable, when placed on a skin site to be treated, by electrical connection to the electrical power supply to both the first and second electrodes, thereby to trigger the electrochemical oxidation or reduction of the inactive precursor substance on one of the electrodes to produce a physiologically or antimicrobially active oxidised or reduced compound which is capable of diffusing towards the skin site for the treatment thereof.

2. The skin dressing according to claim 1, wherein the electrodes are sheet-like and substantially planar.

3. The skin dressing according to claim 2, wherein the electrodes have a thickness of less than 1.0 mm.

4. The skin dressing according to claim 1, wherein the electrodes are co-planar.

5. The skin dressing according to claim 4, wherein one electrode substantially surrounds the other electrode.

6. The skin dressing according to claim 1, wherein the ratio of the surface area of the first electrode to the second electrode is at least 2:1.

7. The skin dressing according to claim 1, wherein at least one electrode comprises multiple strands or elements, which are spread apart from each other.

8. The skin dressing according to claim 1, wherein the electrodes are non-metallic.

9. The skin dressing according to claim 8, wherein the electrodes are made from carbon.

10. The skin dressing according to claim 1, wherein the inactive precursor substance comprises an iodide salt.

11. The skin dressing according to claim 1, wherein the inactive precursor substance comprises a sulphate salt.

12. The skin dressing according to claim 1, wherein the potential difference applied to the electrodes is from 1 to 10 volts.

13. The skin dressing according to claim 1, further comprising an insulating tab configured for removal from the electrodes, wherein removal makes the electrical connection to the electrical power supply.

14. A packaged skin dressing comprising the skin dressing according to claim 13 and packaging enclosing the skin dressing, wherein the removal of the insulating tab is effected by removal of the skin dressing from its packaging.

15. The skin dressing according to claim 1, which also comprises a skin-contacting layer which acts as a reservoir of the inactive precursor substance, is a diffusion medium for the produced active compound and physically separates the electrodes from the skin site.

16. The skin dressing according to claim 15, wherein the skin-contacting layer is in the form of a sheet, layer or film.

17. The skin dressing according to claim 16, wherein the sheet, layer or film has a thickness in the range 0.01 to 2.0 mm.

18. The skin dressing according to claim 15, wherein the skin-contacting layer is in a hydrated condition containing sufficient water for an electrochemical circuit to be formed and for the produced active compound to diffuse through the skin-contacting layer and to the skin site.

19. The skin dressing according to claim 15, wherein the skin-contacting layer is in the form of a hydrogel, a sponge, a foam or a hydrophilic matrix that can hold sufficient water to allow a controlled diffusion path from the electrodes to the skin site.

20. A method of applying a skin dressing to a skin site, the method comprising:
- providing a skin dressing comprising first and second electrodes, an electrical power supply not electrically connected to at least one of the first and second electrodes, and an inactive precursor substance;
- placing the skin dressing on the skin site;
- connecting the electrical power supply to at least one of the first and second electrodes to form an electrochemical circuit; and
- producing a physiologically or antimicrobially active compound by electrochemical oxidation or reduction of the inactive precursor substance on one of the first electrode and the second electrode.

* * * * *